United States Patent
Dellinger et al.

(10) Patent No.: US 7,368,550 B2
(45) Date of Patent: May 6, 2008

(54) PHOSPHORUS PROTECTING GROUPS

(75) Inventors: Douglas J Dellinger, Boulder, CO (US); Zoltan Timar, Boulder, CO (US); Geraldine Dellinger, Boulder, CO (US); Marvin H Caruthers, Boulder, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/388,339

(22) Filed: Mar. 23, 2006

(65) Prior Publication Data

US 2007/0099859 A1    May 3, 2007

Related U.S. Application Data

(60) Provisional application No. 60/731,723, filed on Oct. 31, 2005.

(51) Int. Cl.
*C07H 21/00*    (2006.01)

(52) U.S. Cl. .................. 536/23.1; 536/25.31; 536/26.7; 536/26.8

(58) Field of Classification Search ................ None
See application file for complete search history.

(56) References Cited

U.S. PATENT DOCUMENTS 6,335,437 B1 *    1/2002    Manoharan ................ 536/25.3

\* cited by examiner

*Primary Examiner*—L. E. Crane

(57) ABSTRACT

Compounds having a phosphorus group structure of:

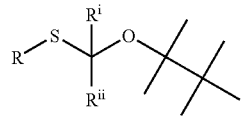

wherein:
  R is alkyl, modified lower alkyl; and
  $R^i$ and $R^i$ are each independently H, alkyl, modified alkyl, or aryl; are provided. Also provided are polynucleotide compositions that include these compounds and methods of using the compounds in synthesis of the same.

19 Claims, No Drawings

PHOSPHORUS PROTECTING GROUPS

RELATED APPLICATIONS

Related subject matter is disclosed in U.S. Patent Application filed by Dellinger et al. entitled "Monomer Compositions for the Synthesis of Polynucleotides, Methods of Synthesis, and Methods of Deprotection" and, now U.S. patent application Ser. No. 11/387,388; U.S. Patent Application filed by Dellinger et al. entitled "Monomer Compositions for the Synthesis of Polynucleotides, Methods of Synthesis, and Methods of Deprotection" and, now U.S. patent application Ser. No. 11/388,112; U.S. Patent Application filed by Dellinger et al. entitled "Solutions, Methods, and Processes for Deprotection of Polynucleotides" and, now U.S. patent application Ser. No. 11/387,369; U.S. Patent Application filed by Dellinger et al. entitled "Use of Mildly Basic Solutions of Peroxyanions for the Post-Synthesis Deprotection of RNA Molecules and Novel Monomer Compositions for the Synthesis of RNA" and, now U.S. Provisional Application No. 60/785,130; U.S. Patent Application filed by Dellinger et al. entitled "Cleavable Linkers for Polynucleotides" and, now U.S. patent application Ser. No. 11/389,388; U.S. Patent Application filed by Dellinger et al. entitled "Thiocarbonate Linkers for Polynucleotides" and, now U.S. patent application Ser. No. 11/751,692; all above-mentioned patent applications filed on the same day as the present application. Related subject matter is also disclosed in U.S. Provisional Patent Application filed on Oct. 31, 2005 by Dellinger et al. entitled "Methods for Deprotecting Polynucleotides" having Ser. No. 60/731,723 filed Oct. 31, 2005

FIELD OF THE INVENTION

The invention relates generally to nucleic acid chemistry. More particularly, the invention relates to providing protecting groups useful in polynucleotide synthesis, as well as other uses.

BACKGROUND OF THE INVENTION

Over the past twenty years, the method of choice for the chemical synthesis of oligonucleotides (ONs) has been the phosphoramidite four-step process which utilizes the reaction of deoxynucleoside phosphoramidites with a solid phase tethered nucleoside or oligonucleotide (Letsinger, R. L.; Lunsford, W. B. *J. Am. Chem. Soc.* 1976, 98, 3655-3661; Beaucage, S. L.; Caruthers, M. H. *Tetrahedron Lett.* 1981, 22, 1859-1862; Matteucci, M. D.; Caruthers, M. H. *J. Am. Chem. Soc.* 1981, 103, 3186-3191).

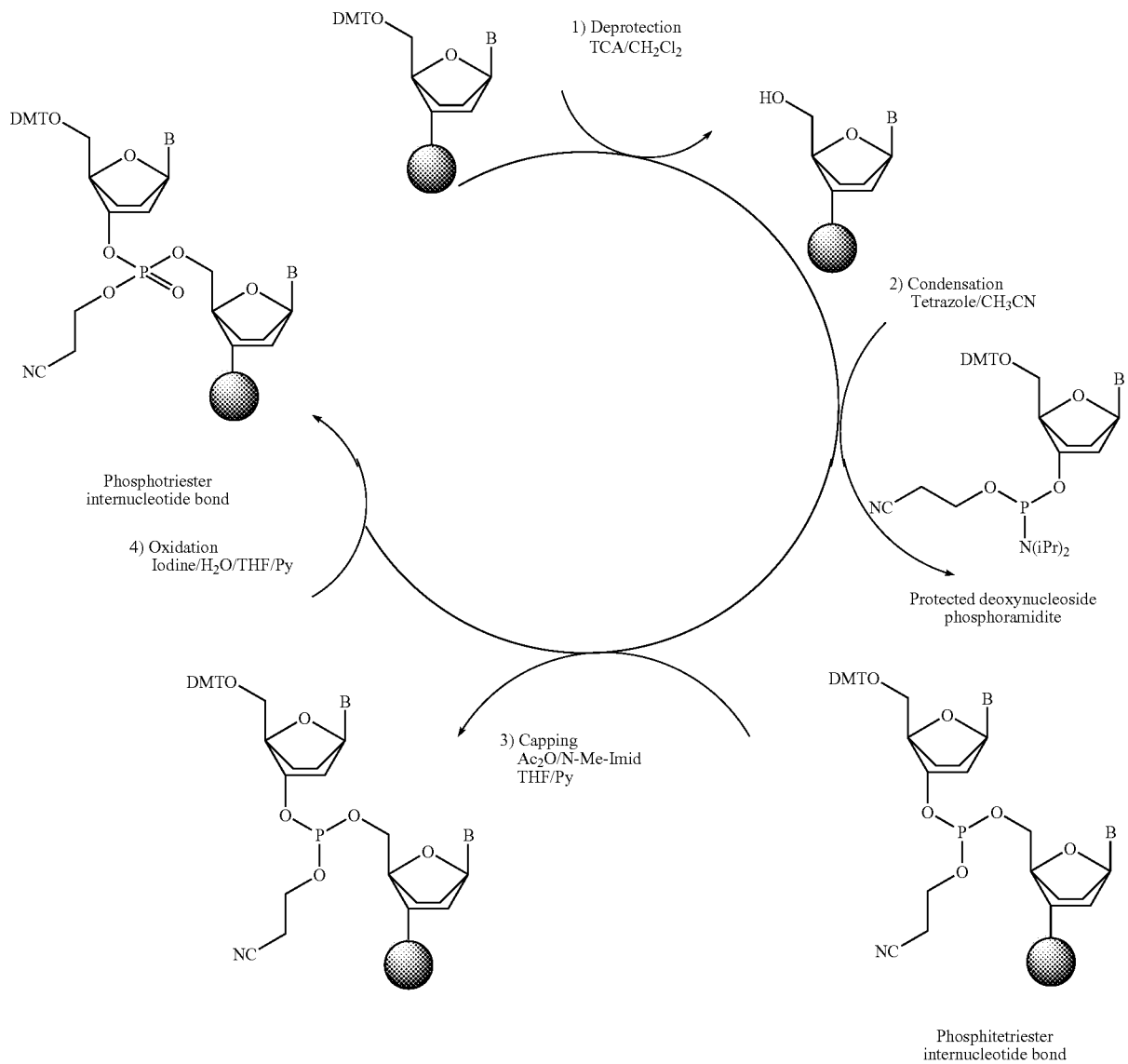

Initially the 5'-O-dimethoxytrityl (DMT) group is removed from a deoxynucleoside linked to the polymer support. Step 2, elongation of a growing oligodeoxynucleotide, occurs via the initial formation of a phosphite triester internucleotide bond. This reaction product is first treated with a capping agent designed to esterify failure sequences and cleave phosphite reaction products on the heterocyclic bases. The nascent phosphite internucleotide linkage is then oxidized to the corresponding phosphotriester. In the final step of each cycle, the DMT group is removed from the growing oligonucleotide using a large excess of a weak acid, trichloroacetic acid (TCA), in an organic solvent. Further repetitions of this four-step process generate the ON of desired length and sequence. The final product is cleaved from the solid phase and obtained free of base and the β-cyanoethylphosphate (Sinha, N. D.; Biernat, J.; Koster, H., *Tetrahedron Lett.* 1983, 24, 5843-5846) protecting groups by treatment of the support with concentrated ammonium hydroxide, methyl amine or other nucleophillic strong bases (Ogilvie, K. K.; Theriault, N. Y.; Seifert, J-M.; Pon, R. T.; Nemer, J. J. *Can. J Chem.* 1980, 58, 2686-26930).

We have recently developed a new method of deprotection of oligonucleotides that does not require strong bases like ammonia or methyl amine. This method utilizes the strong nucleophilicity of peroxyanions at mildly basic pH. This is especially applicable to the chemical synthesis of oligoribonucleotides (RNA). Since this method has many significant advantages for the deprotection of oligonucleotides, it is especially appropriate to develop protecting groups that are specifically designed to utilize these novel deprotection conditions. Although many of the standard protecting groups in the prior art can be removed using these novel conditions, those standard protecting groups were optimized for removal using strong bases. In addition, several of the standard protecting groups require strong bases. A clear example of this is the β-cyanoethylphosphate protecting group. This group is typically removed by a β-elimination reaction (see U.S. Pat. Re34,069 to Koster et al.). The typical β-elimination reaction occurs by having an electron withdrawing group in the α-position to a methylene carbon. This makes the protons of the α-methylene group acidic and they can thereby be removed using a strong base. The compound then eliminates the phosphate in the β-position and forms an alkene such as acryonitrile.

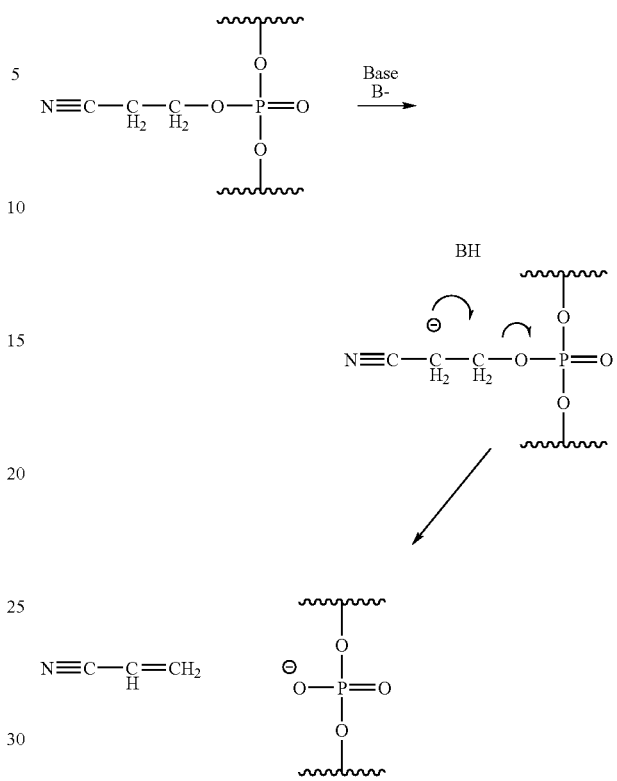

Although this works well for the use of a strong base like ammonia, we typically use peroxyanion solutions at pH conditions below 11. At this pH the proton cannot easily be abstracted, and these β-elminination reactions are not well suited for use with peroxyanions.

The use of strongly electron withdrawing groups such as the cyanoethyl groups has the additional disadvantage of deactivating the phosphoramidite reagent toward coupling of the internucleotide bond. This is especially important in the chemical synthesis of RNA. In typical RNA synthesis the 2'-hydroxyl is protected creating additional inhibition of coupling by crowding around the reactive phosphorus center.

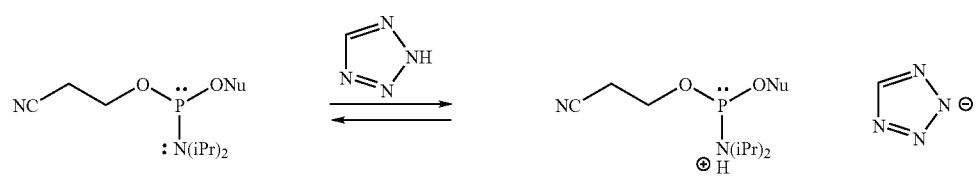

Nu = Nucleoside

-continued

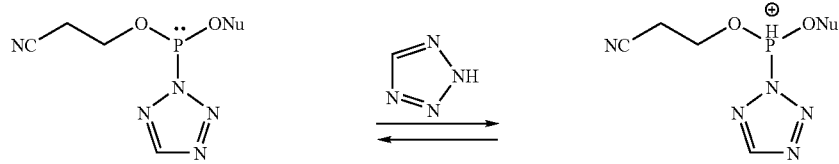

As shown above, protonation by azole acid catalysts followed by nitrogen exchange converts the phosphite species to several highly active electrophiles. An electron withdrawing protecting group can significantly decrease the reactivity of the active intermediates. This inhibition is made worse by the crowding around the active phosphorus reagent that occurs in the chemical synthesis of RNA as a result of the protected 2'-hydroxyl (—OR in the following scheme).

In typical embodiments, the phosphorus protecting group is characterized as being labile under conditions which include an α-effect nucleophile. Also, in typical embodiments, methods are provided comprising contacting a polynucleotide having a phosphorus protecting group with a solution comprising an α-effect nucleophile to result in cleavage of the phosphorus protecting group.

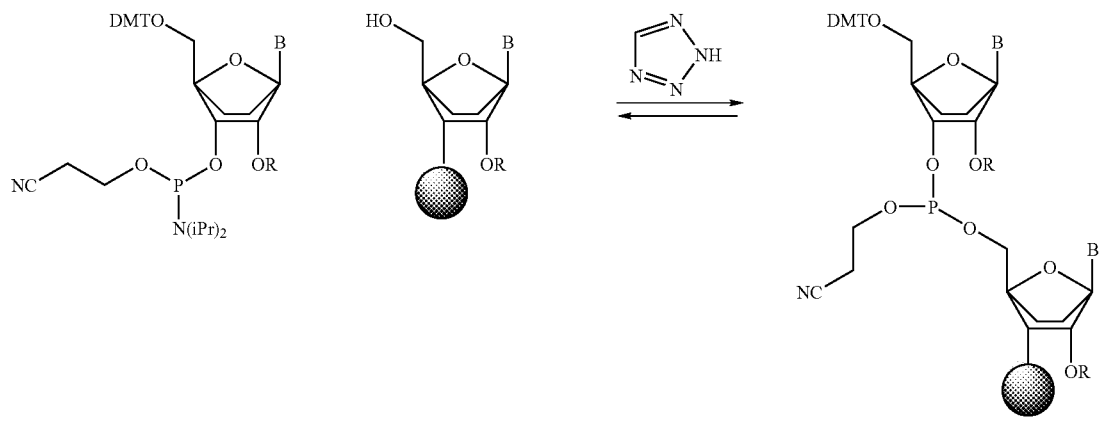

While there are examples of phosphorus protecting groups in the literature, there remains a need for novel phosphorus protecting groups for polynucleotides, e.g. for use during polynucleotide synthesis.

SUMMARY OF THE INVENTION

In certain embodiments of the invention, novel compositions having a phosphorus group and a phosphorus protecting group bound to the phosphorus group are provided, and methods of deprotecting the phosphorus group are provided. In certain embodiments, the phosphorus protecting group has the structure

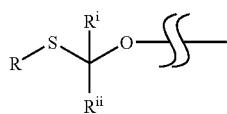

(V)

wherein:
R is lower alkyl, modified lower alkyl, or alkyl;
$R^i$ and $R^{ii}$ are each independently selected from H, lower alkyl, modified lower alkyl, alkyl, modified alkyl, or aryl; and
the broken line indicates a bond to the phosphorus group.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the materials and methods particularly pointed out in the appended claims.

DETAILED DESCRIPTION

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "an insoluble support" includes a plurality of insoluble supports. Similarly, reference to "a substituent", as in a compound substituted with "a substituent", includes the possibility of substitution with more than one substituent, wherein the substituents may be the same or different. In this specification and in the claims that follow, reference will be made to a number of terms that shall be defined to have the following meanings unless a contrary intention is apparent:

A "nucleotide" refers to a sub-unit of a nucleic acid (whether DNA or RNA or analogue thereof) which includes a phosphate group, a sugar group and a heterocyclic base, as well as analogs of such sub-units. A "nucleoside" references a nucleic acid subunit including a sugar group and a heterocyclic base. A "nucleoside moiety" refers to a portion of a molecule having a sugar group and a heterocyclic base (as in a nucleoside); the molecule of which the nucleoside moiety is a portion may be, e.g. a polynucleotide, oligonucleotide, or nucleoside phosphoramidite. A "nucleobase" references the heterocyclic base of a nucleoside or nucleotide. An "optionally protected nucleobase" references the heterocyclic base of a nucleoside or nucleotide, wherein the heterocyclic base optionally has bound thereto a protecting group, e.g. bound to an imine nitrogen of the heterocyclic base or to an exocyclic amine group of the heterocyclic base. A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer. A "polynucleotide moiety" references a moiety that has at least two nucleotide subunits. A "polynucleotide intermediate" references a molecule occurring between steps in chemical synthesis of a polynucleotide, where the polynucleotide intermediate is subjected to further reactions to get the intended final product, e.g. a phosphite intermediate which is oxidized to a phosphate in a later step in the synthesis, or a protected polynucleotide which is then deprotected.

As used herein, polynucleotides include single or multiple stranded configurations, where one or more of the strands may or may not be completely aligned with another. The terms "polynucleotide" and "oligonucleotide" are generic to polydeoxynucleotides (containing 2-deoxy-D-ribose), to polyribonucleotides (containing D-ribose), to any other type of polynucleotide having nucleotide subunits that are N-glycosides of a purine or pyrimidine base, and to other polymers in which the conventional backbone has been replaced with a non-naturally occurring or synthetic backbone or in which one or more of the conventional bases has been replaced with a non-naturally occurring or synthetic base. An "oligonucleotide" generally refers to a nucleotide multimer of about 2 to 200 nucleotides in length, while a "polynucleotide" includes a nucleotide multimer having at least two nucleotides and up to several thousand (e.g. 5000, or 10,000) nucleotides in length. It will be appreciated that, as used herein, the terms "nucleoside", "nucleoside moiety" and "nucleotide" will include those moieties which contain not only the naturally occurring purine and pyrimidine bases, e.g. adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof). Such modifications include, e.g., methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, $N^6$-methyladenine, $N^6$-isopentyladenine, 2-methylthio-$N^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl) uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

"Upstream" as used herein refers to the 5' direction along a polynucleotide, e.g. a DNA or RNA molecule, relative to a point of reference, e.g. a particular nucleotide moiety. "Downstream" refers to the 3' direction along the polynucleotide relative to a point of reference. Hence, a downstream moiety is located in the 3' direction along the polynucleotide. Similarly, an upstream moiety is located at (or is bound to) a nucleotide moiety that is located in the 5' direction along the polynucleotide. The point of reference will often be implied from context or may be generally disposed relative to the referenced element, e.g. an upstream element is located in the 5' direction of any downstream element, and a downstream element is located in the 3' direction of any upstream element. "3'-" and "5'-" relate to the position on a sugar group of a nucleoside moiety and may reference the noted group most closely related to the position, e.g. a 3'-O is the oxygen bound to the 3'-C of the sugar group, further e.g. a 3'-phosphorus reference the phosphorus most closely bound to the 3'-C of the sugar group (i.e. the 3'-phosphorus is the phosphorus of the phospho group bound to the 3'-C of the sugar group). A 3'-terminal nucleotide moiety of a polynucleotide moiety is the nucleotide moiety at the most 3' end of the polynucleotide moiety; in typical embodiments, an adjacent nucleotide moiety is bound to the polynucleotide moiety having the 3'-terminal nucleotide moiety via the 3'-terminal nucleotide moiety, e.g. via an internucleotide bond. Similarly, a 5'-terminal nucleotide moiety of a polynucleotide moiety is the nucleotide moiety at the most 5' end of the polynucleotide moiety; in typical embodiments, an adjacent nucleotide moiety is bound to the polynucleotide moiety having the 5'-terminal nucleotide moiety via the 5'-terminal nucleotide moiety, e.g. via an internucleotide bond.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

The term "modified alkyl" refers to an alkyl group having from one to twenty-four carbon atoms, and further having additional groups, such as one or more linkages selected from ether-, thio-, amino-, phospho-, oxo-, ester-, and amido-, and/or being substituted with one or more additional groups including lower alkyl, aryl, alkoxy, thioalkyl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl. The term "modified lower alkyl" refers to a group having from one to eight carbon atoms and further having additional groups, such as one or more linkages selected from ether-, thio-, amino-, phospho-, keto-, ester- and amido-, and/or being substituted with one or more groups including lower alkyl; aryl, alkoxy, thioalkyl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl. The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above.

The term "alkenyl" as used herein, unless otherwise specified, refers to a branched, unbranched or cyclic (e.g. in the case of C5 and C6) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to eight carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to eight carbon atoms, and includes, for example, acetylenyl and propynyl, and the term "cycloalkynyl" refers to cyclic alkynyl groups.

The term "aryl" as used herein refers to an aromatic species containing 1 to 5 aromatic rings, either fused or linked, and either unsubstituted or substituted with 1 or more substituents typically selected from the group consisting of lower alkyl, modified lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl; and lower alkyl substituted with one or more groups selected from lower alkyl, alkoxy, thioalkyl, hydroxyl thio, mercapto, amino, imino, halo, cyano, nitro, nitroso, azido, carboxy, sulfide, sulfone, sulfoxy, phosphoryl, silyl, silyloxy, and boronyl. Typical aryl groups contain 1 to 3 fused aromatic rings, and more typical aryl groups contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —(CH2)j-Ar wherein j is an integer in the range of 1 to 24, more typically 1 to 6, and Ar is a monocyclic aryl moiety.

The term "heterocyclic" refers to a five- or six-membered monocyclic structure or to an eight- to eleven-membered bicyclic structure which is either saturated or unsaturated. The heterocyclic groups herein may be aliphatic or aromatic. Each heterocyclic group consists of carbon atoms and from one to four heteroatoms selected from the group consisting of nitrogen, oxygen and sulfur. As used herein, the term "nitrogen heteroatoms" includes any oxidized form of nitrogen and the quaternized form of nitrogen. The term "sulfur heteroatoms" includes any oxidized form of sulfur. Examples of heterocyclic groups include purine, pyrimidine, piperidinyl, morpholinyl and pyrrolidinyl. "Heterocyclic base" refers to any natural or non-natural heterocyclic moiety that can participate in base pairing or base stacking interaction on an oligonucleotide strand.

An "internucleotide bond" refers to a chemical linkage between two nucleoside moieties, such as a phosphodiester linkage in nucleic acids found in nature, or such as linkages well known from the art of synthesis of nucleic acids and nucleic acid analogues. An internucleotide bond may comprise a phosphate or phosphite group, and may include linkages where one or more oxygen atoms of the phosphate or phosphite group are either modified with a substituent or replaced with another atom, e.g. a sulfur atom or the nitrogen atom of a mono- or di-alkyl amino group.

The term "halo" or "halogen" is used in its conventional sense to refer to a chloro, bromo, fluoro or iodo substituent.

When used herein, the terms "hemiacetal", "thiohemiacetal", "acetal", and "thioacetal" are art-recognized, and refer to a chemical moiety in which a single carbon atom is geminally disubstituted with either two oxygen atoms or a combination of an oxygen atom and a sulfur atom. In addition, when using the terms, it is understood that the carbon atom may be geminally disubstituted by two carbon atoms, forming ketal compounds. The terms "hemiacetal", "thiohemiacetal", "acetal", and "thioacetal" are generic to the corresponding ketal compounds (respectively, "hemiketal", "thiohemiketal", "ketal", and "thioketal").

A "phospho" group includes a phosphodiester, phosphotriester, and H-phosphonate groups. In the case of either a phospho or phosphite group, a chemical moiety other than a substituted 5-membered furyl ring may be attached to O of the phospho or phosphite group which links between the furyl ring and the P atom.

By "protecting group" as used herein is meant a species which prevents a portion of a molecule from undergoing a specific chemical reaction, but which is removable from the molecule following completion of that reaction, as taught for example in Greene, et al., "Protective Groups in Organic Synthesis," John Wiley and Sons, Second Edition, 1991. A "peroxyanion-labile linking group" is a linking group that releases a linked group when contacted with a solution containing peroxyanions. Similarly, a "peroxyanion-labile protecting group" is a protecting group that is removed from the corresponding protected group when contacted with a solution containing peroxyanions. As used herein, "2'-O protecting groups" or "2'-hydroxyl protecting groups" are protecting groups which protect the 2'-hydroxyl groups of the polynucleotide (e.g. bound to the 2'-O). As used herein, "phosphorus protecting group" (sometimes referenced as "phosphate protecting group") references a protecting group which protects a phosphorus group (e.g. is bound to a phosphorus group wherein the phosphorus group is attached to a sugar moiety of, e.g. a nucleotide, a nucleoside phosphoramidite, a polynucleotide intermediate, or a polynucleotide). As used herein, "cleaving", "cleavage", "deprotecting", "releasing", or like terms when used in reference to a protecting group refers to breaking a bond via which the protecting group is bound to the protected group, resulting in the cleaved protecting group and the deprotected moiety (the moiety that was the protected group when bound to the protecting group).

The term "electron withdrawing" denotes the tendency of a substituent to attract valence electrons of the molecule of which it is a part, i.e., an electron-withdrawing substituent is electronegative with respect to neighboring atoms. A quantification of the level of electron-withdrawing capability is given by the Hammett sigma constant. This well known constant is described in many references, for instance, March, Advanced Organic Chemistry 251-59, McGraw Hill Book Company, New York, (1977). Exemplary electron-withdrawing groups include nitro, acyl, formyl, sulfonyl, trifluoromethyl, cyano, chloride, and the like.

The term "electron-donating" refers to the tendency of a substituent to repel valence electrons from neighboring atoms, i.e., the substituent is less electronegative with respect to neighboring atoms. Exemplary electron-donating groups include amino, methoxy, alkyl (including alkyl having a linear or branched structure, alkyl having one to eight carbons), cycloalkyl (including cycloalkyl having four to nine carbons), and the like.

The term "alpha effect," as in an "alpha effect nucleophile" in a deprotection/oxidation agent, is used to refer to an enhancement of nucleophilicity that is found when the atom adjacent a nucleophilic site bears a lone pair of electrons. As the term is used herein, a nucleophile is said to exhibit an "alpha effect" if it displays a positive deviation from a Bronsted-type nucleophilicity plot. Hoz et al. (1985) Israel J. Chem. 26:313. See also, Aubort et al. (1970) Chem. Comm. 1378; Brown et al. (1979) J. Chem. Soc. Chem. Comm.171; Buncel et al. (1982) J. Am. Chem. Soc. 104: 4896; Edwards et al. (1962) J. Am. Chem. Soc. 84:16; Evanseck et al. (1987) J. Am. Chem Soc. 109:2349. The magnitude of the alpha effect is dependent upon the electrophile which is paired with the specific nucleophile. McIsaac, Jr. et al. (1972), J. Org. Chem. 37:1037. Peroxy anions are example of nucleophiles which exhibit strong alpha effects.

"Moiety" and "group" are used interchangeably herein to refer to a portion of a molecule, typically having a particular functional or structural feature, e.g. a linking group (a portion of a molecule connecting two other portions of the molecule), or an ethyl moiety (a portion of a molecule with a structure closely related to ethane).

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phosphate (—PO$_4$H—), ester (—O—C(O)—).

"Bound" may be used herein to indicate direct or indirect attachment. In the context of chemical structures, "bound" (or "bonded") may refer to the existence of a chemical bond directly joining two moieties or indirectly joining two moieties (e.g. via a linking group). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect.

"Functionalized" references a process whereby a material is modified to have a specific moiety bound to the material, e.g. a molecule or substrate is modified to have the specific moiety; the material (e.g. molecule or support) that has been so modified is referred to as a functionalized material (e.g. functionalized molecule or functionalized support).

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group.

"Substituent" references a group that replaces another group in a chemical structure. Typical substituents include nonhydrogen atoms (e.g. halogens), functional groups (such as, but not limited to amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include alkyl, lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, boronyl, and modified lower alkyl.

A "group" includes both substituted and unsubstituted forms. Typical substituents include one or more lower alkyl, amino, imino, amido, alkylamino, arylamino, alkoxy, aryloxy, thio, alkylthio, arylthio, alkyl; aryl, thioalkyl, hydroxyl, mercapto, halo, cyano, nitro, nitroso, azido, carboxy, sulfide, sulfonyl, sulfoxy, phosphoryl, silyl, silyloxy, and boronyl optionally substituted on one or more available carbon atoms with a nonhydrocarbyl substituent such as cyano, nitro, halogen, hydroxyl, sulfonic acid, sulfate, phosphonic acid, phosphate, or phosphonate or the like. Any substituents are typically chosen so as not to substantially adversely affect reaction yield (for example, not lower it by more than 20% (or 10%, or 5% or 1%) of the yield otherwise obtained without a particular substituent or substituent combination).

As used herein, "dissociation constant", e.g. an acid dissociation constant, has its conventional definition as used in the chemical arts and references a characteristic property of a molecule having a tendency to lose a hydrogen ion. The value of a dissociation constant mentioned herein is typically expressed as a negative $\log_{10}$ value, i.e. a pKa (for an acid dissociation constant).

Hyphens, or dashes, are used at various points throughout this specification to indicate attachment, e.g. where two named groups are immediately adjacent a dash in the text, this indicates the two named groups are attached to each other. Similarly, a series of named groups with dashes between each of the named groups in the text indicates the named groups are attached to each other in the order shown. Also, a single named group adjacent a dash in the text indicates the named group is typically attached to some other, unnamed group. In some embodiments, the attachment indicated by a dash may be, e.g. a covalent bond between the adjacent named groups. In some other embodiments, the dash may indicate indirect attachment, i.e. with intervening groups between the named groups. At various points throughout the specification a group may be set forth in the text with or without an adjacent dash, (e.g. amido or amido-, further e.g. Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g. where a linkage is intended, such as linking groups).

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

We have now developed compositions which have phosphorus protecting groups. The phosphorus protecting groups are characterized as being labile upon contact with an α-effect nucleophile. Thus, in certain embodiments, methods of cleaving the phosphorus protecting groups using an α-effect nucleophile are provided. In various embodiments of the invention, novel compositions comprising a polynucleotide bound to a phosphorus protecting group are provided. In certain embodiments, novel compositions comprising a nucleoside phosphoramidite having a phosphorus protecting group are provided. In some embodiments, methods of removing a phosphorus protecting group are provided.

Accordingly, in certain embodiments of the present invention, a composition is provided having a structure selected from structure (I) or structure (II):

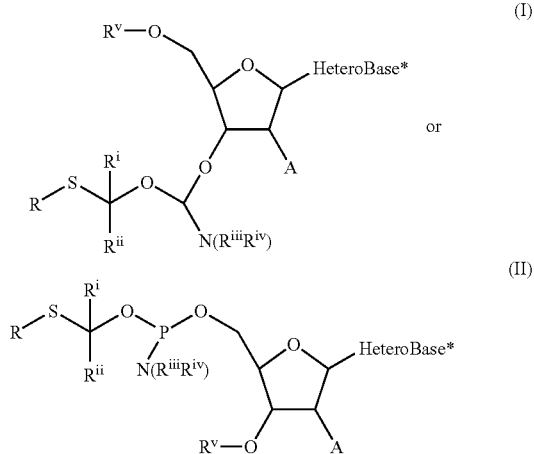

or a salt, conjugate base, or ionized form thereof, wherein:
HeteroBase* is an optionally protected nucleobase;
A is H, OH, or a 2'-hydroxyl protecting group;
R is lower alkyl, modified lower alkyl, or alkyl;
$R^i$ and $R^{ii}$ are each independently selected from H, lower alkyl, modified lower alkyl, alkyl, modified alkyl, or aryl;
$R^{iii}$ and $R^{iv}$ are each independently selected from lower alkyl, or $R^{iii}$ and $R^{iv}$ taken together are cycloalkyl; and
$R^v$ is H, a hydroxyl protecting group, a nucleotide moiety, or an oligonucleotide moiety.

In embodiments in which $R^v$ is a hydroxyl protecting group, the hydroxyl protecting group at the 3' or 5' position ($R^v$) may be any hydroxyl protecting group known in the art of polynucleotide synthesis. The hydroxyl protecting group at the 3' or 5' position should be selected to be compatible with the intended use of the composition, e.g. compatible with a selected synthesis method. Particularly contemplated are protecting groups known for their use in the 4-step phosphoramidite synthesis methods, e.g. trityl or modified trityl (e.g. monomethoxytrityl, dimethoxytrityl, etc.)

In typical embodiments, $R^v$ is a hydroxyl protecting group, and the composition of structure (I) or structure (II) is a nucleoside 3'-phosphoramidite monomer or a nucleoside 5'-phosphoramidite monomer, respectively.

In certain embodiments, $R^v$ is a nucleotide moiety or an oligonucleotide moiety, and the composition of structure (I) or structure (II) is an oligonucleotide phosphoramidite. Such embodiments typically arise in certain polynucleotide synthesis schemes which involve adding small oligonucleotides during each round of synthesis (rather than a single nucleotide), or may be used to attach an oligonucleotide to a substrate or to another oligonucleotide.

In particular embodiments, a composition having a structure selected from structure (I) or structure (II) is provided in which A is a 2'-hydroxyl protecting group, R is selected from methyl, ethyl, n-propyl, or isopropyl; $R^i$ and $R^{ii}$ are each independently selected from H, methyl, ethyl, n-propyl, or isopropyl; $R^{iii}$ and $R^{iv}$ are each isopropyl; and $R^v$ is a hydroxyl protecting group. In certain embodiments, $R^i$ and $R^{ii}$ are each independently selected from H, lower alkyl, alkyl, or aryl.

In certain embodiments, a polynucleotide is provided having a phosphorus protecting group in accordance with the present invention. Such a polynucleotide typically has a series of nucleotide subunits bound to each other, at least one of the nucleotide subunits having the structure (III):

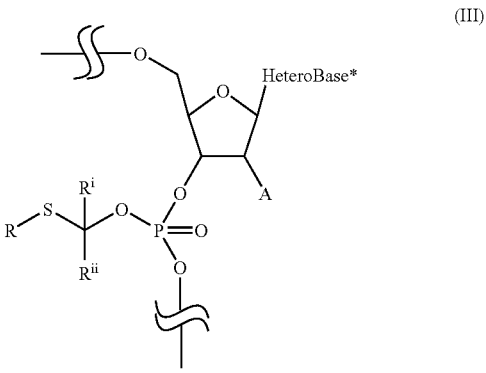

wherein:
HeteroBase* is an optionally protected nucleobase;

A is H, OH, or a 2'-hydroxyl protecting group;

R is lower alkyl, modified lower alkyl, or alkyl;

$R^i$ and $R^{ii}$ are each independently selected from H, lower alkyl, modified lower alkyl, alkyl, modified alkyl, or aryl; and the broken lines indicate sites of attachment to the remainder of the polynucleotide.

Regarding the nucleotide subunit having the structure (III), in particular embodiments A is a 2'-hydroxyl protecting group, R is selected from methyl, ethyl, n-propyl, or isopropyl; and $R^i$ and $R^{ii}$ are each independently selected from H, methyl, ethyl, n-propyl, or isopropyl. In certain embodiments, $R^i$ and $R^{ii}$ are each independently selected from H, lower alkyl, alkyl, or aryl.

In certain such embodiments, a polynucleotide is provided having the structure (IV):

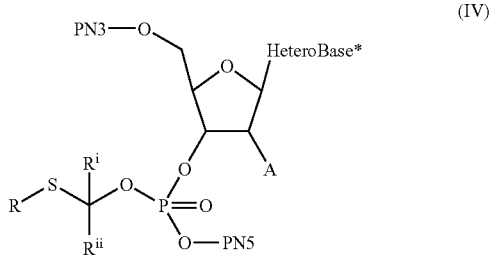

(IV)

wherein:

HeteroBase* is an optionally protected nucleobase;

A is H, OH, or a 2'-hydroxyl protecting group;

R is lower alkyl, modified lower alkyl, or alkyl;

$R^i$ and $R^{ii}$ are each independently selected from H, lower alkyl, modified lower alkyl, alkyl, modified alkyl, or aryl;

PN3 is polynucleotide moiety; and

PN5 is polynucleotide moiety.

PN3 is an upstream polynucleotide moiety, i.e. PN3 is upstream of the remainder of the polynucleotide having the structure (IV). The upstream polynucleotide moiety PN3 has a 3'-terminal nucleotide moiety, the 3'-terminal nucleotide moiety bound to the 5'-O of structure (IV); i.e. the 3'-terminal nucleotide moiety has a 3'-phosphorus, the 5'-O of structure (IV) bound to the 3'-phosphorus of the 3'-terminal nucleotide moiety, i.e. to form a phosphotriester linkage. PN5 is downstream polynucleotide moiety, i.e PN5 is downstream of the remainder of the polynucleotide having the structure (IV). The downstream polynucleotide moiety PN5 has a 5'-terminal nucleotide moiety, the 5'-terminal nucleotide moiety bound to the indicated phosphate oxygen of structure (IV); i.e. the 5'-terminal nucleotide moiety has a 5'-carbon, the 5' carbon of the 5'-terminal nucleotide moiety bound to the indicated phosphate oxygen of structure (IV), i.e. to form a phosphotriester linkage. The upstream polynucleotide moiety PN3 may be any polynucleotide moiety having at least two nucleotide subunits. Similarly, the downstream polynucleotide moiety PN5 may be any polynucleotide moiety having at least two nucleotide subunits. The upstream polynucleotide moiety PN3 is attached to the downstream polynucleotide moiety PN5 via a nucleotide subunit having the structure (III).

The 2'-hydroxyl protecting group (designated "A" in structures (I), (II), (III), and (IV) ) may be any hydroxyl protecting group known in the art of polynucleotide synthesis. The 2'-hydroxyl protecting group should be selected to be compatible with the intended use of the composition, e.g. compatible with a selected synthesis method. In this regard, "compatible" means that the protecting groups are stable under conditions required, e.g. in the selected synthesis method, labile under conditions required for deprotection, and which do not otherwise significantly interfere with the intended use. Particularly contemplated are the 2'-hydroxyl protecting groups described in copending application filed on the same day as the present application by Dellinger et al. entitled "Monomer Compositions for the Synthesis of Polynucleotides, Methods of Synthesis, and Methods of Deprotection" and, now U.S. patent application Ser. No. 11/388,112, and U.S. Patent Application filed by Dellinger et al. entitled "Solutions, Methods, and Processes for Deprotection of Polynucleotides" and, now U.S. patent application Ser. No. 11/387,369.

In certain embodiments, a polynucleotide is provided having a plurality of nucleotide subunits, at least one of said plurality of nucleotide subunits bound to a phosphorus protecting group, the phosphorus protecting group having the structure (V):

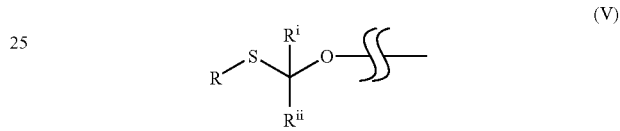

(V)

wherein:

R is lower alkyl, modified lower alkyl, or alkyl;

$R^i$ and $R^{ii}$ are each independently selected from H, lower alkyl, modified lower alkyl, alkyl, modified alkyl, or aryl; and the broken line indicates a bond to said at least one of said plurality of nucleotide subunits.

The broken line in structure (V) indicates the site at which the phosphorus protecting group is bound to a phosphorus which is bound to a 5'-O, a 3'-O, or both a 5'-O and a 3'-O (e.g. the phosphorus part of an internucleotide bond).

In particular embodiments that have a phosphorus protecting group having the structure (V), R may be selected from methyl, ethyl, n-propyl, or isopropyl; and $R^i$ and $R^{ii}$ may each be independently selected from H, methyl, ethyl, n-propyl, or isopropyl. In certain embodiments, $R^i$ and $R^{ii}$ are each independently selected from H, lower alkyl, alkyl, or aryl.

In particular embodiments, more than 50% of all of the nucleotide subunits of a polynucleotide are bound to a phosphorus protecting group according to the present invention, and contacting the polynucleotide with a solution comprising an α-effect nucleophile as described herein results in cleavage of the phosphorus protecting groups to result in the deprotected polynucleotide (the polynucleotide from which phosphorus protecting groups have been removed).

The polynucleotide may be any polynucleotide, for example DNA, RNA, a polynucleotide analog, a modified polynucleotide, a polynucleotide having protecting groups (e.g. protecting groups bound to the amine groups of nucleobases, protecting groups bound to the phosphate groups of the polynucleotide, protecting groups which protect hydroxyl groups of the polynucleotide (e.g. bound to the 2'-O, 3'-O, or 5'-O), or other protecting groups).

In certain embodiments the polynucleotide may be attached to the substrate, e.g. via a cleavable linker. The polynucleotide may be synthesized in situ (e.g. synthesized one nucleotide at a time using polynucleotide synthesis schemes well known in the art) or may be separately synthesized and then attached to the substrate. The polynucleotide may generally be attached to the substrate via any available site of the polynucleotide, e.g. at the 2'-O, the 3'-O, the 5'-O, an amino group of a nucleobase, or any other site. Typically, the polynucleotide is attached to the substrate at the 2'-O or the 3'-O, less typically at the 5'-O or at an amino group of a nucleobase.

In certain embodiments, the polynucleotide may be attached to the substrate via a linking group, which may be any group that is bound to both the substrate and the polynucleotide and which doesn't interfere with the manufacture or use of the polynucleotide. A typical linking group may be selected from (1) a lower alkyl group; (2) a modified lower alkyl group in which one or more linkages selected from ether-, thio-, amino-, oxo-, ester-, and amido- is present; (3) a modified lower alkyl substituted with one or more groups including lower alkyl; aryl, aralkyl, alkoxyl, thioalkyl, hydroxyl, amino, amido, sulfonyl, halo; or (4) a modified lower alkyl substituted with one or more groups including lower alkyl; alkoxyl, thioalkyl, hydroxyl, amino, amido, sulfonyl, halo, and in which one or more linkages selected from ether-, thio-, amino-, oxo-, ester-, and amido- is present. The linking group —Lnk— may be bonded to the substrate at any position of the linking group —Lnk— available to bind to the substrate. Similarly, the linking group —Lnk— may be bonded to the adjacent polynucleotide at any position of the linking group —Lnk— available to bind to the adjacent polynucleotide. In certain embodiments, the linking group —Lnk— is a single methylene group, —$CH_2$—, or may be an alkyl group or modified alkyl group up to about 24 carbons long (and which may be straight-chain or branched-chain). In certain such embodiments, one or more linkages selected from ether-, oxo-, thio-, and amino- is present in the straight-or branched chain modified alkyl group. In an embodiment, the linking group —Lnk— comprises optionally substituted ethoxy, propoxy, or butoxy groups (i.e. may include the structure —{($CH_2$)m—O}n—, wherein m is a integer selected from 2, 3, 4, and n is a integer selected from 1,2,3, 4, 5, 6). In an embodiment, the linking group —Lnk— has the structure —($CH_2$)m-Lkg-($CH_2$)n—, wherein m and n are integers independently selected from the range of 1 to about 12, e.g. from the range of 2 to about 8, and Lkg is a linkage selected from ether-, thio-, amino-, oxo-, ester-, and amido-.

In particular embodiments, the linking group —Lnk—has a first terminal site and a second terminal site. In such embodiments, the linking group —Lnk—is bound to the substrate at the first terminal site, and the linking group —Lnk—is bound to the cleavable linker at the second terminal site. The first and second terminal sites will depend on the design of the linking group taking into consideration, for example, the method used to attach the cleavable linker to the substrate.

The substrate may have a variety of forms and compositions. The substrate may derive from naturally occurring materials, naturally occurring materials that have been synthetically modified, or synthetic materials. Examples of suitable support materials include, but are not limited to, nitrocellulose, glasses, silicas, teflons, and metals (e.g., gold, platinum, and the like). Suitable materials also include polymeric materials, including plastics (for example, polytetrafluoroethylene, polypropylene, polystyrene, polycarbonate, and blends thereof, and the like), polysaccharides such as agarose (e.g., that available commercially as Sepharose®, from Pharmacia) and dextran (e.g., those available commercially under the tradenames Sephadex® and Sephacyl®, also from Pharmacia), polyacrylamides, polystyrenes, polyvinyl alcohols, copolymers of hydroxyethyl methacrylate and methyl methacrylate, and the like.

The polynucleotide may be bound directly to the substrate (e.g. to the surface of the substrate, e.g. to a functional group on the surface) or indirectly bound to the substrate, e.g. via one or more intermediate moieties (e.g. linking groups) and/or surface modification layer on the substrate. The nature of the site on the substrate to which the polynucleotide is attached (e.g. directly or via a linking group) is not essential to the present invention, as any known coupling chemistry compatible with the substrate (i.e. which doesn't result in significant degradation of the substrate) may be used to couple to the cleavable linker. As such, various strategies of coupling the polynucleotide to a substrate using functional groups on the substrate are known in the art and may be employed advantageously in the disclosed methods. Typical strategies require a complementary reactive group on the polynucleotide (or linking group bound to the polynucleotide) or are selected based on moieties already present on the polynucleotide (or linking group bound to the polynucleotide) (e.g. amino groups, hydroxyl groups, or other functional groups), for example an active group on the substrate that is capable of reacting with a corresponding reactive group attached to the polynucleotide (or linking group bound to the polynucleotide) to result in the polynucleotide bound to the substrate.

Accordingly, in certain embodiments of the present invention, a method is provided wherein the method includes: contacting a polynucleotide with a solution comprising an α-effect nucleophile, wherein the polynucleotide comprises a plurality of nucleotide subunits, at least one of said plurality of nucleotide subunits bound to a phosphorus protecting group, the phosphorus protecting group having the structure (V):

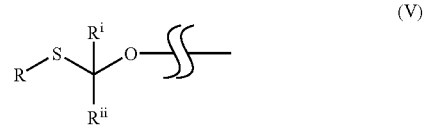

wherein:

R is lower alkyl, modified lower alkyl, or alkyl;

$R^i$ and $R^{ii}$ are each independently selected from H, lower alkyl, modified lower alkyl, alkyl, modified alkyl, or aryl; and the broken line indicates a bond to said at least one of said plurality of nucleotide subunits;

said contacting resulting in cleavage of the phosphorus protecting group from said at least one of said plurality of nucleotide subunits.

Thus, in particular embodiments of the present invention, a method of deprotecting a polynucleotide is provided, the method comprising contacting the polynucleotide with a solution comprising an α-effect nucleophile, wherein the polynucleotide comprises a phosphorus group and a phosphorus protecting group bound thereto, the phosphorus protecting group having the structure (V):

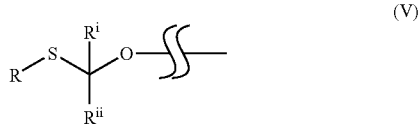

(V)

wherein:
R is lower alkyl, modified lower alkyl, or alkyl;
$R^i$ and $R^{ii}$ are each independently selected from H, lower alkyl, modified lower alkyl, alkyl, modified alkyl, or aryl; and
the broken line indicates a bond to said phosphorus group;
said contacting resulting in cleavage of the phosphorus protecting group from said phosphorus group.

As mentioned above, embodiments of the present disclosure include methods for deprotecting a polynucleotide, wherein the polynucleotide includes a phophorus protecting group such as those described herein. In particular embodiments, the method includes contacting the polynucleotide with a solution of an α-effect nucleophile (e.g., a peroxyanion solution), wherein the α-effect nucleophile has a pKa (negative $\log_{10}$ of the acid dissociation constant) of about 4 to 13. In addition, the solution is at a pH of about 6to 11.

In particular embodiments, a polynucleotide is contacted with a solution of peroxyanions to result in deprotection of the polynucleotide (e.g. cleavage of the phophorus protecting group from the polynucleotide), wherein the peroxyanions have a pKa within the range of about 4 to 12, at neutral to mildly basic pH (e.g. the pH typically is in the range from about 6 to about 11).

In typical embodiments, the conditions employed for deprotection include contacting the polynucleotide with the solution of the α-effect nucleophile for time sufficient to result in cleavage of the phophorus protecting group. Typical times (duration) for the cleavage reaction range from about 15 minutes to about 24 hour, although times outside this range may be used. Typically the duration of the contacting is in the range from about 30 minutes to about 16 hours, e.g. from about 45 minutes to about 12 hours, from about 1 hour to about 8 hours, or from about 1 hour to about 4 hours.

One advantage of using a neutral to mildly basic (e.g. pH in the range from about 6 to about 11) solution including an α-effect nucleophile is that the solution including an α-effect nucleophile is compatible with standard phosphoramidite methods for polynucleotide synthesis. Further, the deprotected polynucleotides are stable and show little or no degradation for an extended period of time when stored in the solution including the α-effect nucleophile.

In general, the solution including the α-effect nucleophile can be a predominantly buffered aqueous solution or buffered aqueous/organic solution. In certain embodiments, it is convenient and cost effective to recover the deprotected polynucleotide from the mixture of deprotected polynucleotide, cleaved phosphorus protecting groups, and solution of α-effect nucleophile by simple precipitation of the desired polynucleotides directly from the mixture by addition of ethanol to the mixture. Under these conditions, the polynucleotide is pelleted to the bottom of a centrifuge tube and the supernatant containing the α-effect nucleophile removed by simply pouring off the supernatant and rinsing the pellet with fresh ethanol. The deprotected polynucleotide is then isolated by resuspending in a typical buffer for chromatographic purification or direct usage in the biological experiment of interest. Because of the nature of most α-effect nucleophiles, removal from the desired deprotected polynucleotide products is easy, quick, and effective using the ethanol precipitation method. Any other methods of recovering the deprotected polynucleotides may be employed, such as using Micro Bio-Spin™ chromatography columns (BioRad, Hercules, Calif.) for cleanup and purification of polynucleotides (used according to product insert instructions).

The solution including the α-effect nucleophile typically may have a pH in the range of about 4 to 11, about 5 to 11, about 6 to 11, about 7 to 11, about 8 to 11, about 4 to 10, about 5 to 10, about 6 to 10, about 7 to 10, or about 8 to 10. In particular embodiments the solution has a pH of about 7 to 10. It should also be noted that the pH is dependent, at least in part, upon the α-effect nucleophile in the solution and the protecting groups on the polynucleotide. Appropriate adjustments to the pH can be made to the solution to accommodate the α-effect nucleophile.

The α-effect nucleophiles can include, but are not limited to, peroxyanions, hydroxylamine derivatives, hydroximic acid and derivatives thererof, hydroxamic acid and derivatives thereof, carbazide and semicarbazides and derivatives thereof. The α-effect nucleophiles can include compounds such as, but not limited to, hydrogen peroxide, peracids, perboric acid salts, alkylperoxides, hydrogen peroxide salts, hydroperoxides, butylhydroperoxide, benzylhydroperoxide, phenylhydroperoxide, cumene hydroperoxide, performic acid, peracetic acid, perbenzoic acid and substituted perbenzoic acids such as chloroperbenzoic acid, perbutyric acid, tertiary-butylperoxybenzoic acid, decanediperoxoic acid, other similar compounds, and all corresponding salts, and combinations thereof. Hydrogen peroxide, salts of hydrogen peroxide and mixtures of hydrogen peroxide and performic acid are especially useful. Hydrogen peroxide, whose pKa is around 11, is particularly useful in solutions above pH 9.0. Below pH 9.0 there is no significant concentration of peroxyanion to work as an effective nucleophile. Below pH 9.0 it is especially useful to use mixtures of hydrogen peroxide and peracids. These peracids can be preformed and added to the solution or they can be formed in situ by the reaction of hydrogen peroxide and the carboxylic acid or carboxylic acid salt. An example is that an equal molar mixture of hydrogen peroxide and sodium formate can be used at pH conditions below 9.0 as an effective α-effect nucleophile solution where hydrogen peroxide alone is not provide a high concentration of α-effect nucleophiles. The utility of peracids tends to be dependent upon the pKa of the acid and size of molecule: the higher the pKa of the acid the more useful as a peroxyanion solution, the larger the size of the molecule the less useful. Typically the pKa of the peracid is lower than the pH of the desired peroxyanion solution.

The α-effect nucleophiles typically used in these reactions are typically strong oxidants, therefore one should limit the concentration of the reagent in the solution in order to avoid oxidative side products where undesired. The α-effect nucleophiles are typically less than 30% weight/vol of the solution, more typically between 0.1% and 10% weight/vol of the solution and most typically 3% to 7% weight/vol of the solution. The typical 3% solution of hydrogen peroxide is about 1 molar hydrogen peroxide. A solution of between 1 molar and 2 molar hydrogen peroxide is typically useful. A typical solution of hydrogen peroxide and performic acid is an equal molar mixture of hydrogen peroxide and performic acid, both in the range of 1 to 2 molar. An example of an in situ prepared solution of performic acid is 2 molar hydrogen peroxide and 2 molar sodium formate buffered at pH 8.5.

In typical embodiments, the α-effect nucleophile is characterized as having a pKa in the range from about 4 to 13, about 4 to 12, about 4 to 11, about 5 to 13, about 5 to 12, about 5 to 11, about 6 to 13, about 6 to 12, about 6 to 11, about 7 to 13, about 7 to 12, or about 7 to 11.

It should also be noted that the dissociation constant (the pKa) is a physical constant that is characteristic of the specific α-effect nucleophile. Chemical substitution and solvent conditions can be used to raise or lower the effective dissociation constant and therefore specifically optimize the conditions under which the deprotection of the polynucleotide is performed (to result in release of the phosphorus protecting group from the polynucleotide, and, optionally, deprotection of other groups protected by peroxyanion-labile protecting groups). Appropriate selection of the α-effect nucleophile should be made considering the other conditions of the method and the protecting groups of the polynucleotide. In addition, mixtures of carboxylic acids and hydroperoxides can be used to form salts of peracids in situ.

As an example a solution of hydrogen peroxide can be used with a solution of formic acid at pH conditions below 9.0. At pH conditions less than 9.0 hydrogen peroxide is not significantly ionized due to its pKa of around 11. At pH 7.0 only about 0.01% of the hydrogen peroxide is in the ionized form of the α-effect nucleophile. However, the hydrogen peroxide can react in situ with the formic acid to form performic acid in a stable equilibrium. At pH 7.0 the performic acid is significantly in the ionized form and is an active α-effect nucleophile. The advantage of such an approach is that solutions of performic acid tend to degrade rapidly and stabilizers need to be added. The equilibrium that is formed between the hydrogen peroxide solutions and the formic acid helps stabilize the performic acid such that it can be used to completely cleave the polynucleotides from the substrates prior to degrading. Performic acid is especially useful in a buffered mixture of hydrogen peroxide at pH 8.5 because the pKa of performic acid is approximately 7.1. Peracetic acid is useful at pH 8.5 but less useful than performic acid because the pKa of peracetic acid is approximately 8.2. At pH 8.5 peracetic acid is only about 50% anionic whereas at pH 8.5 performic acid is more than 90% anionic.

In general, the pKa for the hydroperoxides is about 8 to 13. The pKa for hydrogen peroxide is quoted to be about 10 to 12 depending upon the method of analysis and solvent conditions. The pKa for the alkylperoxides is about 8 to 14. The pKa for the peracids is about 3 to 9. In some embodiments in which the peroxyanion is hydroperoxide, the solution is at pH of about 9 to 11, e.g. at a pH of about 9 to about 10. In certain embodiments in which the peroxyanion is an alkylperoxide, the solution is at pH of about 8 to 11. In embodiments where the peroxyanion is a peracid, the solution is at pH of about 6 to 9. In addition, the peracid typically has a pKa of about 4 to 10.

In addition, the aqueous buffer solution usually includes a buffer, such as, but not limited to, tris(hydroxymethyl)aminomethane, aminomethylpropanol, citric acid, N,N'-Bis(2-hydroxyethyl)glycine, 2-[Bis(2-hydroxyethyl)amino]-2-(hydroxy-methyl)-1,3-propanediol, 2-(Cyclohexylamino)ethane-2-sulfonic acid, N-2-Hydroxyethyl)piperazine-N'-2-ethane sulfonic acid, N-(2-Hydroxyethyl)piperazine-N'-3-propane sulfonic acid, Morpholinoethane sulfonic acid, Morpholinopropane sulfonic acid, Piperazine-N,N'-bis(2-ethane sulfonic acid), N-Tris(hydroxymethyl)methyl-3-aminopropane sulfonic acid, N-Tris(hydroxymethyl)methyl-2-aminoethane sulfonic acid, N-Tris(hydroxymethyl)methylglycine, and combinations thereof.

One significant potential advantage for removing the phosphorus protecting group from the polynucleotide according to the present methods is that the α-effect nucleophile solution can be exploited to remove a variety of peroxyanion-labile protecting groups at the same time and under the same conditions that are used to cleave the phosphorus protecting group from the polynucleotide. Thus, cleavage of the phosphorus protecting group from the polynucleotide and deprotection of groups protected with peroxyanion-labile protecting groups may be reduced to a single step in which the phosphorus group deprotection and deprotection of other sites on the polynucleotide (e.g. 2'-OH, nucleobase) occur at essentially the same time in the same reaction mixture. These advantages become even more significant if they are used with the protecting groups described in the applications cited herein to Dellinger et al. that were filed on the same day as the present application; such protecting groups specifically provide for rapid deprotection under the oxidative, nucleophilic conditions at neutral to mildly basic pH.

Particularly contemplated is the use of the cleavable linkers described in the two U.S. patent applications filed by Dellinger et al. on the same day as the instant application (one entitled "Cleavable Linkers for Polynucleotides" and, now U.S. patent application Ser. No. 11/389,388; the second entitled "Thiocarbonate Linkers for Polynucleotides" and now U.S. patent application Ser. No. 11/751,692 in conjunction with phosphorus protecting groups attached to the polynucleotide as described herein. Optionally, peroxyanion-labile protecting groups may be attached, e.g. at the 2'-position of the nucleoside sugar of the individual nucleotide subunits, at the exocyclic amine groups of the heterocyclic bases of the polynucleotide, and/or at the imine groups of the heterocyclic bases of the polynucleotide. In certain such embodiments, contacting the polynucleotide with solution including an α-effect nucleophile results in concurrent cleavage of the polynucleotide from the substrate and deprotection of the polynucleotide at the phosphate groups, as well as (optionally) deprotection at the 2'-position of the nucleoside sugar, at the exocyclic amine groups, and/or at the imine groups of the heterocyclic bases.

In particular embodiments a polynucleotide having a phosphorus protecting group as described herein has peroxyanion-labile protecting groups on, e.g. the exocyclic amine groups of the nucleobases. In some such embodiments, contacting the polynucleotide with solution including an α-effect nucleophile results in concurrent deprotection of the phosphate groups and of the exocyclic amine groups. As another example, in particular embodiments a polynucleotide having a phosphorus protecting group as described herein has peroxyanion-labile protecting groups on, e.g. the 2' position of the nucleoside sugar. In certain such embodiments, contacting the polynucleotide with a solution including an α-effect nucleophile results in concurrent deprotection of the phosphate groups and of the 2' position of the nucleoside sugar (e.g. resulting in a deprotected 2'-hydroxyl group). In a further example, a polynucleotide having a phosphorus protecting group has peroxyanion-labile protecting groups on, e.g. the 2' position of the nucleoside sugar and the exocyclic amine groups. In certain such embodiments, contacting the polynucleotide with a solution including an α-effect nucleophile results in concurrent deprotection of the phosphate groups, of the 2' position of the nucleoside sugar, and of the exocyclic amine groups. In certain embodiments such as those described above, the polynucleotide having a phosphorus protecting group as described herein is bound to a substrate via a cleavable linker, wherein the cleavable linker is labile upon contact with an α-effect nucleophile. In certain such embodiments, contacting the polynucleotide with a solution including an α-effect nucleophile results in concurrent cleavage of the polynucleotide from the substrate as well as deprotection of the phosphate groups, and (optionally) of the 2' position of the nucleoside sugar, and (optionally) of the exocyclic amine groups.

Structure (VII) serves to illustrate a portion of a polynucleotide bound to a substrate, and illustrates that there are several sites of the polynucleotide which may have protecting groups bound thereto, including phosphorus protecting groups (designated R in structure (VII), and sometimes referenced herein as "phosphate protecting groups"), nucleobase protecting groups (designated R' in structure (VII)); and 2'-hydroxyl protecting groups (designated R' in structure (VII), and sometimes referenced herein as 2'-O protecting groups). Note that structure (VII) only depicts two nucleotide subunits, but that typically there will be many more nucleotide subunits in the polynucleotide having the same general structure as the nucleotide subunits depicted in structure (VII). In structure (VII), B represents a nucleobase. It is contemplated that, in particular embodiments, the phosphorus protecting groups (R in structure (VII)) described herein may be labile under the same conditions that result in removal of other protecting groups (i.e. R' and/or R") as well as cleavage of the cleavable linkers (CLG in structure (VII)) via which the polynucleotide is attached to a substrate.

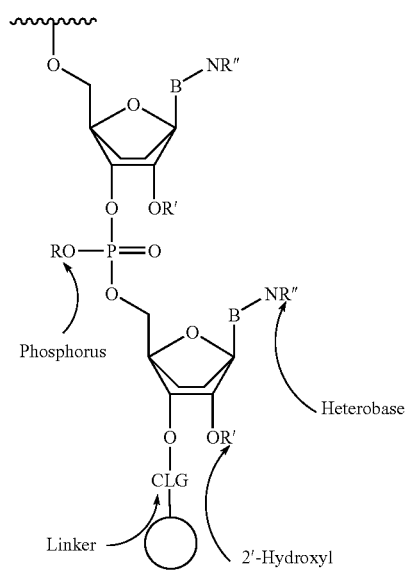

(VII)

In particular embodiments the polynucleotide has a plurality of phosphate groups wherein each phosphate group is bound to a phosphorus protecting group as described herein. The phosphorus protecting group is labile upon being contacted with a solution of an α-effect nucleophile (e.g. the phosphorus protecting group is peroxyanion-labile). In certain embodiments, a cleavable linker is used that is also labile upon being contacted with the solution of the α-effect nucleophile. Thus, the cleavable linker may be cleaved and the phosphate groups may undergo deprotection concurrently upon being contacted with a solution comprising an α-effect nucleophile. Examples of such cleavable linkers are described in a copending application filed on the same day as the instant application by Dellinger et al. entitled entitled "Cleavable Linkers for Polynucleotides" and, now U.S. patent application Ser. No. 11/389,388, and also in a copending application filed on the same day as the instant application by Dellinger et al. entitled "Thiocarbonate Linkers for Polynucleotides" and, now U.S. patent application Ser. No. 11/751,692.

Thus, in particular embodiments, the present invention provides for a method that includes: contacting a polynucleotide bound to a substrate via a cleavable linker with a solution comprising an α-effect nucleophile; wherein said cleavable linker is characterized as being labile upon exposure to the α-effect nucleophile; wherein the polynucleotide has a plurality of phosphate groups; wherein each phosphate group of the plurality of phosphate groups has a phosphorus protecting group bound thereto, said phosphorus protecting group having the structure (V):

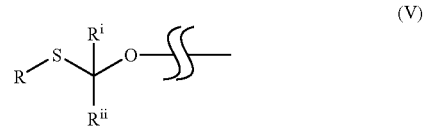

(V)

wherein:

R is lower alkyl, modified lower alkyl, or alkyl;

$R^i$ and $R^{ii}$ are each independently selected from H, lower alkyl, modified lower alkyl, alkyl, modified alkyl, or aryl; and the broken line indicates a bond to said phosphorus group;

said contacting resulting in concurrent cleavage of the polynucleotide from the substrate and deprotection of each phosphate group of the plurality of phosphate groups.

In particular embodiments the polynucleotide has a plurality of nucleobases, wherein each nucleobase is bound to a nucleobase protecting group. In certain such embodiments, the nucleobase protecting group is labile under the same conditions as the phosphorus protecting group (e.g. the nucleobase protecting group is peroxyanion-labile). Thus, the nucleobases and the phosphate groups may undergo deprotection concurrently upon being contacted with a solution comprising an α-effect nucleophile. Any nucleobase protecting group known in the art of polynucleotide synthesis that is labile under conditions of being contacted with the α-effect nucleophile may be used. Examples of such nucleobase protecting groups are described in a copending application filed on the same day as the instant application by Dellinger et al. entitled "Monomer Compositions for the Synthesis of Polynucleotides, Methods of Synthesis, and Methods of Deprotection" and, now U.S. patent application Ser. No. 11/387,388.

Thus, in particular embodiments, the present invention provides for a method that includes: contacting a polynucleotide with a solution comprising an α-effect nucleophile; wherein the polynucleotide has a plurality of nucleobases; wherein each nucleobase of the plurality of nucleobases has a nucleobase protecting group bound thereto, said nucleobase protecting group characterized as being labile upon exposure to the α-effect nucleophile; wherein the polynucleotide has a plurality of phosphate groups; wherein each phosphate group of the plurality of phosphate groups has a phosphorus protecting group bound thereto, said phosphorus protecting group having the structure (V):

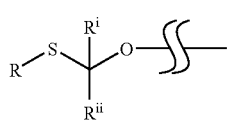

(V)

wherein:

R is lower alkyl, modified lower alkyl, or alkyl;

$R^i$ and $R^{ii}$ are each independently selected from H, lower alkyl, modified lower alkyl, alkyl, modified alkyl, or aryl; and the broken line indicates a bond to said phosphorus group;

said contacting resulting in concurrent deprotection of the plurality of nucleobase and the plurality of phosphate groups.

In particular embodiments the polynucleotide has a plurality of 2'-O groups wherein each 2'-O group is bound to a 2'-O protecting group (i.e. a 2'-hydroxyl protecting group). In certain such embodiments, the 2'-O protecting group is labile under the same conditions as the phosphorus protecting group (e.g. the 2'-O protecting group is peroxyanion-labile). Thus, the phosphate groups and the 2'-O groups may undergo deprotection concurrently upon being contacted with a solution comprising an α-effect nucleophile. Any 2'-O protecting group known in the art of polynucleotide synthesis that is labile under conditions of being contacted with the α-effect nucleophile may be used. Examples of such 2'-O protecting groups are described in a copending application filed on the same day as the instant application by Dellinger et al. entitled "Monomer Compositions for the Synthesis of Polynucleotides, Methods of Synthesis, and Methods of Deprotection" and, now U.S. patent application Ser. No. 11/388,112.

Thus, in particular embodiments, the present invention provides for a method that includes: contacting a polynucleotide with a solution comprising an α-effect nucleophile; wherein the polynucleotide has a plurality of 2'-O groups; wherein each 2'-O group of the plurality of 2'-O groups has a 2'-O protecting group bound thereto, said 2'-O protecting group characterized as being labile upon exposure to the α-effect nucleophile; wherein the polynucleotide has a plurality of phosphate groups; wherein each phosphate group of the plurality of phosphate groups has a phosphorus protecting group bound thereto, said phosphorus protecting group having the structure (V):

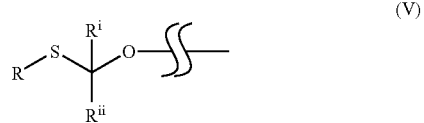

(V)

wherein:

R is lower alkyl, modified lower alkyl, or alkyl;

$R^i$ and $R^{ii}$ are each independently selected from H, lower alkyl, modified lower alkyl, alkyl, modified alkyl, or aryl; and the broken line indicates a bond to said phosphorus group;

said contacting resulting in concurrent deprotection of the plurality of 2'-O groups and the plurality of phosphate groups.

Furthermore, in certain embodiments, the polynucleotide includes a plurality of phosphate groups, a plurality of nucleobases, and a plurality of 2'-O groups. In some embodiments, the polynucleotide also includes one or more (e.g. two or more, e.g. all three) types of protecting groups selected from phosphorus protecting groups, nucleobase protecting groups, or 2'-O protecting groups. Each protecting group is bound to a corresponding site of the polynucleotide (i.e. phosphorus protecting groups are bound to phosphate groups, nucleobase protecting groups are bound to nucleobases, and 2'-O protecting groups are bound to 2'-O groups). In certain embodiments, the polynucleotide is bound to a substrate via a cleavable linker, and the method provides for deprotection of the polynucleotide and concurrent cleavage of the polynucleotide from the substrate. The concurrent deprotection and cleavage may include deprotection of: 1) the phosphate groups 2) the phosphate groups and the nucleobases, 3) the phosphate groups and the 2'-O groups; or 4) the phosphate groups, the nucleobases, and the 2'-O groups.

Further Examples:

In some embodiments, the present invention provides compositions having phosphorus protecting groups that are phosphate esters of thiohemiacetals. Exemplary compositions are represented by the general formula:

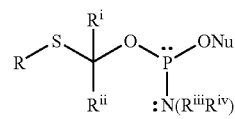

wherein:

R is lower alkyl, modified lower alkyl, or alkyl;

$R^i$ and $R^{ii}$ are each independently selected from H, lower alkyl, modified lower alkyl, alkyl, modified alkyl, or aryl;

$R^{iii}$ and $R^{iv}$ are each independently selected from lower alkyl, or $R^{iii}$ and $R^{iv}$ taken together are cycloalkyl; and Nu is a nucleoside moiety.

Because of the electron donating nature of the thioacetal there is an observed increased reactivity in coupling in the presence of azole acid catalysts, as compared to cyanoethyl protected phosphoramidites.

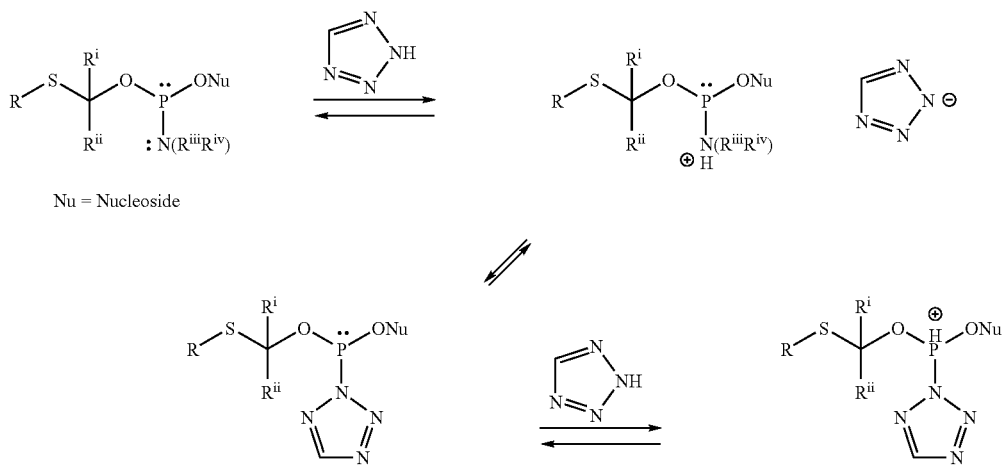

Nu = Nucleoside

This increased reactivity makes these reagents especially useful for the synthesis of RNA as well as other oligonucleotides.

These novel phosphite reagents can either be prepared as halophosphoramidites or bis-aminophosphodiamidites.

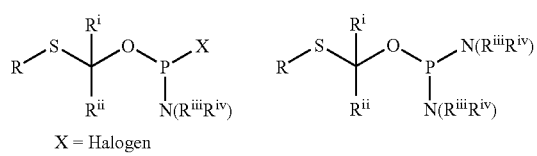

X = Halogen

These active phosphites can be reacted with protected nucleosides to form novel phosphoramidite monomers. Halophosphoramidites are reacted under anhydrous conditions with non-nucleophilic bases to produce the desired protected nucleoside phosphoramidite monomers.

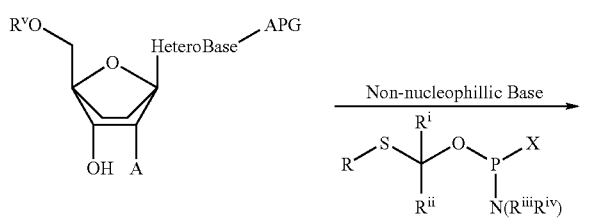

(wherein HeteroBase is a nucleobase; A is a 2'-hydroxyl protecting group; APG is an optional nucleobase protecting group; and $R^v$ is a hydroxyl protecting group).

The bis-aminophosphodiamidites are reacted using azole catalysts or amine salts of azole catalysts (Barone A D, Tang J Y, Caruthers M H, *Nucleic Acids Res.*, 1984, 12(10), 4051-61) to produce the desired protected nucleoside phosphoramidite monomers.

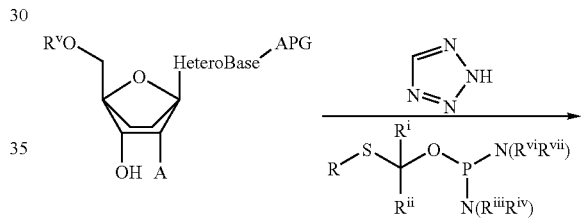

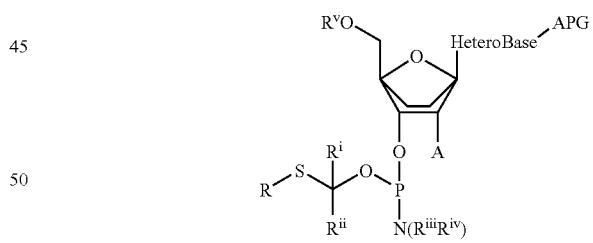

A very useful species in this class is where $R^i$ and $R^{ii}$ are both hydrogen. In this case the thiohemiacetal is quite stabile and can be conveniently prepared from commercial reagents.

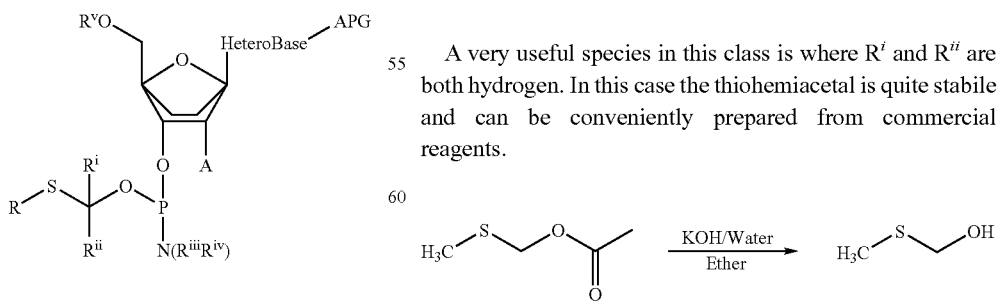

Commercial Reagent

The alcohol can then be converted into a reactive phosphate reagent using standard methods

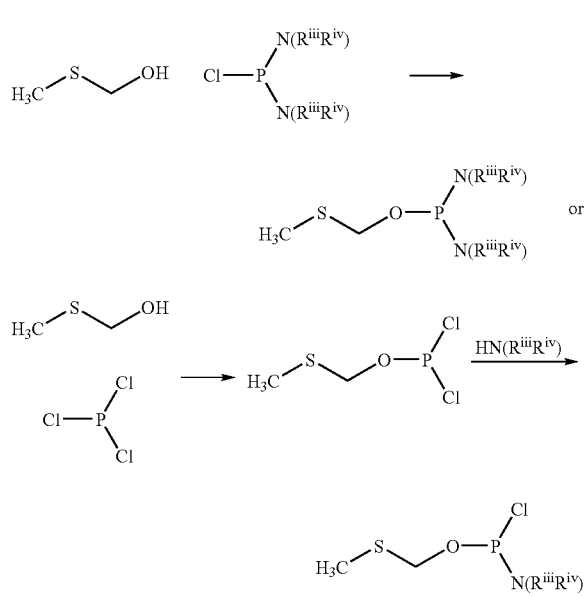

In the case where $R^i$ and $R^{ii}$ are both hydrogen there is less crowding around the active phosphorus center resulting in higher coupling yields. In the case where $R^i$ and $R^{ii}$ are both alkyl or aryl, the thiohemiacetal is less stabile and is best made by condensation of a thiosilane on a ketone or aldehyde as described by Evans et. al. (1997) J. Am. Chem. Soc. 99(15):5009-17:

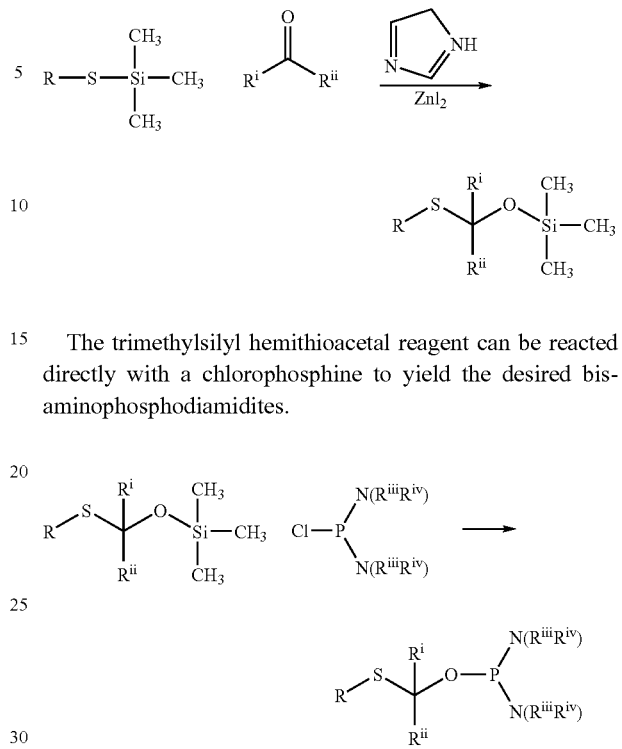

The trimethylsilyl hemithioacetal reagent can be reacted directly with a chlorophosphine to yield the desired bis-aminophosphodiamidites.

Conversion to protected nucleoside phosphoramidite monomers as described above provides reagents which can then be integrated into the standard 4-step synthesis cycle:

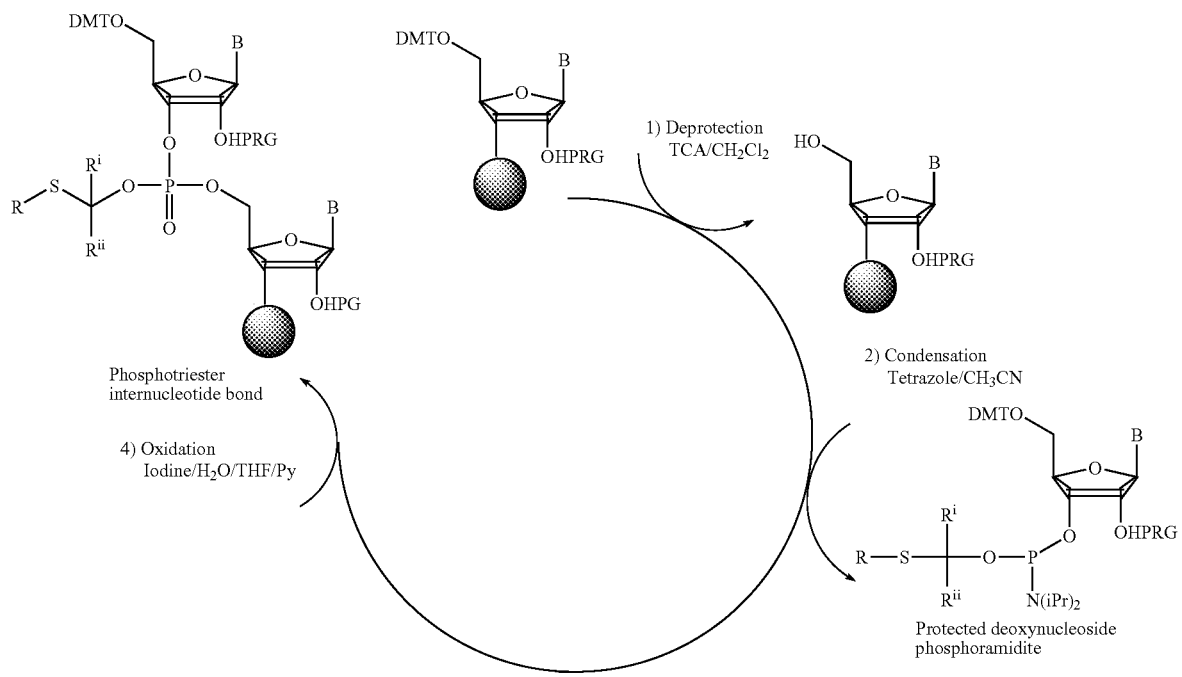

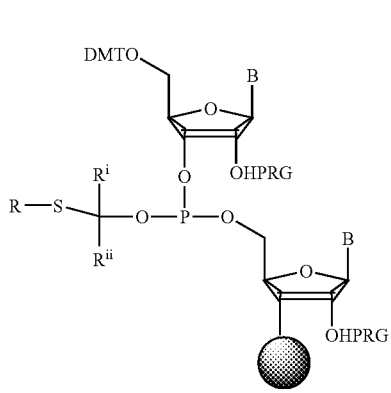 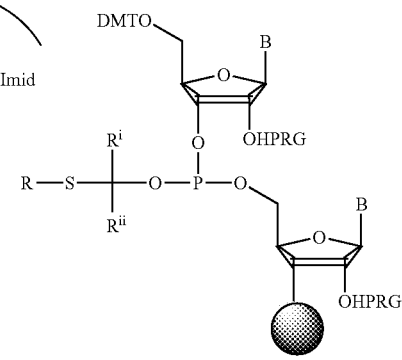

3) Capping
Ac₂O/N-Me-Imid
THF/Py

Phosphitetriester
internucleotide bond

Post synthesis, the oligonucleotides are exposed to a solution of peroxyanions at mildly basic pH. Without limiting the claimed invention, it is believed that the peroxide first oxidizes the sulfur to a sulfoxide then a sulfone. A peroxyanion then cleaves the protecting group and liberates the phosphodiester internucleotide bond. Thus, contacting with the α-effect nucleophile results in deprotection of the phosphate group, giving the deprotected phosphate diester internucleotide linkage.

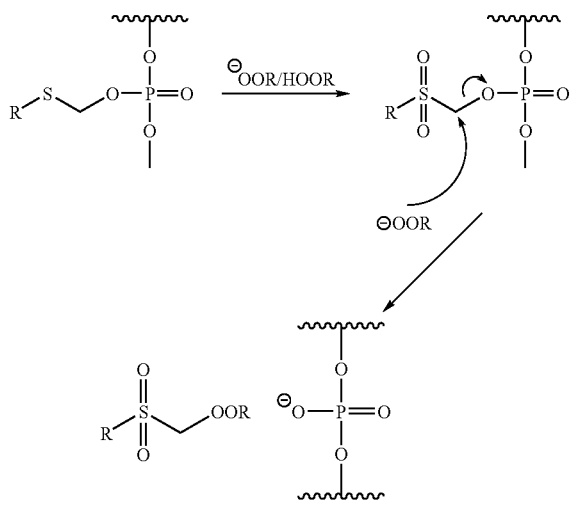

The practice of the present invention will employ, unless otherwise indicated, conventional techniques of synthetic organic chemistry, biochemistry, molecular biology, and the like, which are within the skill of the art. Such techniques are explained fully in the literature.

Experimental:

Synthesis of bis(N,N-diisopropylamino)chlorophosphine:

A 5 L three neck round bottom flask was equipped with a Friedrich's condenser, a ground glass stirrer bearing, a silicon rubber septum, and placed under dry argon. Two liters of anhydrous diisopropylamine (1.6 kg, 15.9 mol) were added to the flask and diluted by addition of two liters anhydrous acetonitrile. The solution was mixed with a mechanical stirrer attached to a glass rod and a Teflon blade. An ice-water bath was placed under the flask and the solution allowed to cool with stirring for 30 min. Phosphorus trichloride (313 g, 2.3 mol) was placed in a dry two liter flask and one liter of anhydrous acetonitrile added. This phosphorus trichloride solution was then added slowly by cannulation to the vigorously stirred solution of diisopropylamine. Once addition was complete, the ice bath was removed and the reaction mixture stirred overnight. Complete conversion of the phosphorus trichloride (δ 201 ppm) to product (δ 134 ppm) was monitored by $^{31}$P NMR. The reaction mixture was filtered to remove diisopropylamine hydrochloride and the precipitate washed with anhydrous ether. The combined filtrates were concentrated in vacuo to a semi-crystalline solid. Anhydrous hexanes (1.5 L) were added to the flask and the mixture heated. The hot liquid was filtered through a Schlenk filter funnel to remove residual amine hydrochloride and the resulting clear liquid concentrated in vacuo to half the original volume. The product was then isolated by crystallization, filtration, and drying in vacuo to yield 447 g (74% yield). $^{31}$P NMR (CD₃CN) δ 134.4 (s); Electron Impact Mass Spectrometry gave a molecular ion of 267 m/e.

Synthesis of bis(N, N-diisopropylamino)methylthiomethylphosphite:

Acetic acid methylthiomethyl ester (50 mmol) was purchased from TCI America (Portland, Oreg.) and dissolved in 200 mL of ether and 100 mL of a 1.0 M solution of KOH in water added. The reaction was allowed to stir overnight and the ether solution separated, dried over anhydrous sodium sulfate and evaporated to an oil to produce the hemithioacetal. bis(N,N-Diisopropylamino)chlorophosphine (50 mmol) is dissolved in anhydrous acetonitrile with freshly distilled, anhydrous, diisopropylethyl amine (60 mmol). The hemithioacetal is added drop wise and the reaction stirred overnight. The product is evaporated to an oil and the phosphorodiamidite isolated by trituration into pentanes.

General Procedure for the Synthesis of Nucleoside Phosphoramidites:

Protected deoxynucleosides were dissolved in anhydrous dichloromethane at 0.05 to 0.1 M, depending upon their solubility, and 1.2 molar equivalents of the appropriate phosphorodiamidite added with stirring. Upon complete dissolution of the reaction components, 0.8 molar equivalent tetrazole was added to the reaction mixture as a 0.45 M solution in anhydrous acetonitrile. The reaction mixture was allowed to stir for 24 h at room temperature and then analyzed for extent of reaction by $^{31}$P NMR and silica gel TLC (eluted with ethyl acetate). The reaction was determined to be complete by spot to spot conversion to a faster eluting product on TLC and by complete loss of the phosphorodiamdite 31P NMR signal. Upon completion, the reaction was quenched by addition of 0.8 molar equivalents of anhydrous triethylamine. After 5 min, the reaction mixture was concentrated to a viscous oil in vacuo using a rotary evaporator. The viscous oil was redissolved in a minimum volume of ethyl acetate and was added to the top of a silica gel column pre-equilibrated with various mixtures of ethyl acetate:hexanes. Isocratic elution of the column with appropriate solvents for each preparation (monitored by TLC) was used to collect the product. Fractions containing the product were combined and concentrated to a foam in vacuo on a rotary evaporator, redissolved in a minimal amount of anhydrous dichloromethane, and added dropwise to rapidly stirring anhydrous hexanes. The solid precipitate was isolated by filtration and dried overnight in vacuo. The resulting white solids were analyzed by $^{31}$P NMR and FAB mass spectroscopy.

The instant specification is put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, percents are wt./wt., temperature is in ° C. and pressure is at or near atmospheric. Standard temperature and pressure are defined as 20° C. and 1 atmosphere.

A synthesis of reagents used in certain embodiments of the present invention is now described. It will be readily apparent that the reactions described herein may be altered, e.g. by using modified starting materials to provide correspondingly modified products, and that such alteration is within ordinary skill in the art. Given the disclosure herein, one of ordinary skill will be able to practice variations that are encompassed by the description herein without undue experimentation.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties.

What is claimed is:

1. A compound having a structure selected from structure (I) or structure (II):

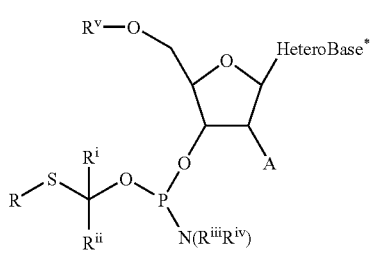

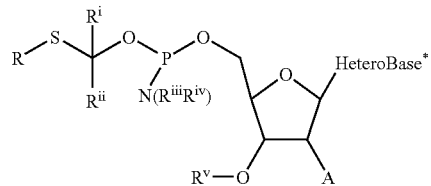

or a salt thereof,
wherein:
HeteroBase* is an optionally protected nucleobase;
A is H, OH, or a protected 2'-hydroxyl group;
R is a modified lower alkyl, or alkyl;
$R^i$ and $R^{ii}$ are each independently H, alkyl, modified alkyl, or aryl;
$R^{iii}$ and $R^{iv}$ are each independently lower alkyl, or $R^{iii}$ and $R^{iv}$ taken together are cycloalkyl; and
$R^v$ is H, a hydroxyl protecting group, a nucleotide moiety, or an oligonucleotide moiety.

2. The compound of claim 1, wherein A is a protected 2'-hydroxyl group, R is methyl, ethyl, n-propyl, or isopropyl; $R^i$ and $R^{ii}$ are each independently H, methyl, ethyl, n-propyl, or isopropyl; $R^{iii}$ and $R^{iv}$ are each isopropyl; and $R^v$ is a hydroxyl protecting group.

3. The compound of claim 1, wherein $R^v$ is a hydroxyl protecting group.

4. A polynucleotide, the polynucleotide comprising at least one nucleotide subunit having the structure (III):

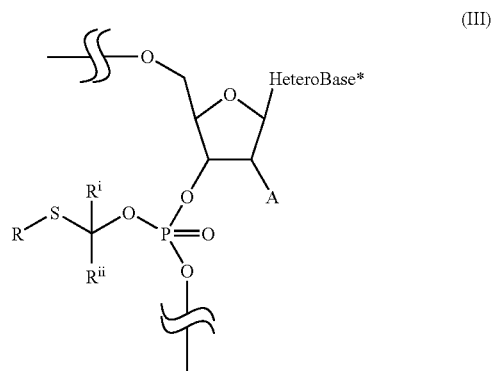

wherein:
HeteroBase* is an optionally protected nucleobase;
A is H, OH, or a protected 2'-hydroxyl group;
R is a modified lower alkyl, or alkyl;
$R^i$ and $R^{ii}$ are each independently H, alkyl, modified alkyl, or aryl; and
the broken lines indicate sites of attachment to the remainder of the polynucleotide.

5. The polynucleotide of claim 4, wherein A is a protected 2'-hydroxyl group, R is selected from methyl, ethyl, n-propyl, or isopropyl; and $R^i$ and $R^{ii}$ are each independently H, methyl, ethyl, n-propyl, or isopropyl.

6. A polynucleotide, the polynucleotide comprising a plurality of nucleotide subunits, at least one of said plurality of nucleotide subunits bound to a phosphorus protecting group, the phosphorus protecting group having the structure (V):

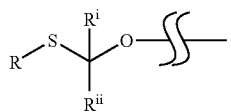

(V)

wherein:
R is modified lower alkyl, or alkyl;
$R^i$ and $R^{ii}$ are each independently H or lower alkyl; and
the broken line indicates a bond to said at least one of said plurality of nucleotide subunits.

7. The polynucleotide of claim 6, wherein R is a methyl, ethyl, n-propyl, or isopropyl; and R1 and R" are each independently H, methyl, ethyl, n-propyl, or isopropyl.

8. The polynucleotide of claim 6, wherein each one of at least 50% of the plurality of nucleotide subunits is bound to a respective phosphorus protecting group, each respective phosphorus protecting group having the structure (V).

9. The polynucleotide of claim 6, wherein the polynucleotide is DNA or RNA.

10. A method of deprotecting a protected polynucleotide, the method comprising;
contacting the polynucleotide with a solution comprising an α-effect nucleophile, wherein the polynucleotide comprises a plurality of nucleotide subunits, at least one of said plurality of nucleotide subunits bound to a phosphorus protecting group, the phosphorus protecting group having the structure (V):

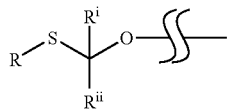

(V)

wherein:
R is a modified lower alkyl, or alkyl;
$R^i$ and $R^{ii}$ are each independently H, alkyl, modified alkyl, or aryl; and
the broken line indicates a bond to said at least one of said plurality of nucleotide subunits;
said contacting resulting in cleavage of the phosphorus protecting group from said at least one of said plurality of nucleotide subunits.

11. The method of claim 10 wherein the solution is at a pH of about 6 to about 11.

12. The method of claim 10 wherein the α-effect nucleophile has a $pK_a$ in the range of about 4 to 13.

13. The method of claim 10 wherein the solution comprising the α-effect nucleophile is a solution comprising one or more species selected from hydrogen peroxide, a peracid, a perboric acid, an alkylperoxide, a hydroperoxide, a butylhyd roperoxide, a benzylhyd roperoxide, a phenylhydroperoxide, a cumene hydroperoxide, performic acid, peracetic acid, perbenzoic acid, a substituted perbenzoic acid, chloroperbenzoic acid, perbutyric acid, tertiary-butylperoxybenzoic acid, decanediperoxoic acid and corresponding salts of said species.

14. The method of claim 10 wherein the solution comprising the α-effect nucleophile is a solution comprising one or more species selected from hydrogen peroxide, salts of hydrogen peroxide, and mixtures of hydrogen peroxide and performic acid.

15. The method of claim 10 wherein the α-effect nucleophile is formed in situ by a reaction of hydrogen peroxide and a carboxylic acid or carboxylic acid salt.

16. The method of claim 10 wherein the α-effect nucleophile has a $pK_a$ of about 4 to 13 and the solution is at a pH in the range from about 6 to about 11.

17. The method of claim 10 wherein the cleavage of the phosphorus protecting group results in a deprotected polynucleotide.

18. The method of claim 10 wherein the cleavage of the phosphorus protecting group results in a solution of deprotected polynucleotide, the method further comprising adding an alcohol to the solution of deprotected polynucleotide to result in precipitation of the deprotected polynucleotide, and recovering the precipitated polynucleotide.

19. The method of claim 10 further comprising wherein the protected polynucleotide is attached to a substrate via a cleavable linker.

* * * * *

UNITED STATES PATENT AND TRADEMARK OFFICE
CERTIFICATE OF CORRECTION

| | | |
|---|---|---|
| PATENT NO. | : 7,368,550 B2 | Page 1 of 1 |
| APPLICATION NO. | : 11/388339 | |
| DATED | : May 6, 2008 | |
| INVENTOR(S) | : Dellinger et al. | |

It is certified that error appears in the above-identified patent and that said Letters Patent is hereby corrected as shown below:

On the Title page, in field (56), under "Abstract", in column 2, line 4 (Excluding Structure), delete "$R^i$" and insert -- $R^{ii}$ --, therefor.

In column 35, line 15, in Claim 7, delete "R1" and insert -- $R^i$ --, therefor.

In column 35, line 15, in Claim 7, delete "R''" and insert -- $R^{ii}$ --, therefor.

In column 35, line 22, in Claim 9, after "DNA" insert -- , --.

In column 35, line 24, in Claim 10, delete "comprising;" and insert -- comprising: --, therefor.

In column 36, line 13, in Claim 13, delete "hyd roperoxide," and insert -- hydroperoxide, --, therefor.

In column 36, line 13, in Claim 13, delete "benzylhyd roperoxide," and insert -- benzylhydroperoxide, --, therefor.

In column 36, line 17, in claim 13, after "acid" insert -- , --.

Signed and Sealed this

Nineteenth Day of August, 2008

JON W. DUDAS
*Director of the United States Patent and Trademark Office*